(12) United States Patent
Wasserman et al.

(10) Patent No.: US 12,263,339 B2
(45) Date of Patent: Apr. 1, 2025

(54) APPARATUSES FOR DELIVERING TUMOR TREATING FIELDS HAVING ELECTRODE ELEMENTS WITH NONUNIFORM THICKNESSES AND METHODS FOR MANUFACTURING SAME

(71) Applicant: Novocure GmbH, Root (CH)

(72) Inventors: Yoram Wasserman, Haifa (IL); Stas Obuchovsky, Haifa (IL); Nataliya Kuplennik, Haifa (IL)

(73) Assignee: Novocure GmbH, Root (CH)

(*) Notice: Subject to any disclaimer, the term of this patent is extended or adjusted under 35 U.S.C. 154(b) by 249 days.

(21) Appl. No.: 17/886,345

(22) Filed: Aug. 11, 2022

(65) Prior Publication Data

US 2023/0051910 A1 Feb. 16, 2023

Related U.S. Application Data

(60) Provisional application No. 63/232,241, filed on Aug. 12, 2021.

(51) Int. Cl.
*A61N 1/04* (2006.01)
*A61N 1/36* (2006.01)
*A61N 1/40* (2006.01)

(52) U.S. Cl.
CPC ....... *A61N 1/36002* (2017.08); *A61N 1/0476* (2013.01); *A61N 1/40* (2013.01)

(58) Field of Classification Search
CPC ..... A61N 1/36002; A61N 1/0476; A61N 1/40
See application file for complete search history.

(56) References Cited

U.S. PATENT DOCUMENTS

| | | | |
|---|---|---|---|
| 7,565,205 B2 | 7/2009 | Palti | |
| 2006/0149341 A1* | 7/2006 | Palti | A61N 1/0492 600/372 |
| 2011/0141649 A1* | 6/2011 | Villemejane | A61N 1/0472 216/33 |
| 2016/0022986 A1* | 1/2016 | Travers | A61N 1/0476 |
| 2019/0133673 A1 | 5/2019 | Boll et al. | |
| 2020/0171297 A1 | 6/2020 | Kirson et al. | |
| 2021/0162228 A1 | 6/2021 | Urman et al. | |
| 2021/0196207 A1* | 7/2021 | Shamir | G06T 7/0012 |

* cited by examiner

*Primary Examiner* — Ankit D Tejani
*Assistant Examiner* — Joshua Brendon Solomon
(74) *Attorney, Agent, or Firm* — McCarter & English, LLP; Michael A. Sartori

(57) ABSTRACT

An apparatus for delivering tumor treating fields to a subject's body. The apparatus comprises: a plurality of electrically coupled electrode elements to be located on a subject's body and able to deliver tumor treating fields to the subject's body, wherein at least one electrode element of the plurality of electrically coupled electrode elements comprises a dielectric layer, the dielectric layer has a first surface to face the subject's body and a second surface opposite the first surface, and at least one of the first surface and the second surface of the dielectric layer is a non-planar surface.

20 Claims, 5 Drawing Sheets

APPARATUSES FOR DELIVERING TUMOR TREATING FIELDS HAVING ELECTRODE ELEMENTS WITH NONUNIFORM THICKNESSES AND METHODS FOR MANUFACTURING SAME

CROSS-REFERENCE TO RELATED APPLICATIONS

This application claims priority to U.S. patent application Ser. No. 63/232,241 filed on Aug. 12, 2021, which is incorporated herein by reference.

BACKGROUND

Tumor treating fields (TTFields) are low intensity (e.g., 1-4 V/cm) alternating electric fields within the intermediate frequency range (e.g., 50 kHz to 1 MHz, such as 50-500 kHz), which may be used to treat tumors as described in U.S. Pat. No. 7,565,205. TTFields therapy is an approved monotreatment for recurrent glioblastoma (GBM) and an approved combination therapy with chemotherapy for newly diagnosed GBM patients. TTFields can also be used to treat tumors in other parts of a subject's body (e.g., lungs, ovaries, pancreas). For example, TTFields therapy is an approved combination therapy with chemotherapy for malignant pleural mesothelioma (MPM). TTFields are induced non-invasively into the region of interest by transducers (e.g., arrays of capacitively coupled electrode elements) placed directly on the patient's body (e.g., using the Novocure Optune™ system), and applying AC voltages between the transducers.

In the context of GBM, the conventional approach for positioning the transducers is to position the first pair of transducers on the front and back of the head, and to position the second pair of transducers on the right and left sides of the head. In the context of treating mesothelioma, a conventional approach for positioning the transducers is to position the first pair of transducers on the front and back of the torso, and to position the second pair of transducers on the right and left sides of the torso. An AC voltage generator applies an AC voltage (e.g., 200 kHz in the context of GBM or 150 kHz in the context of mesothelioma) between the first pair of transducers for a first interval of time (e.g., one second), which generates an electric field with field lines that generally run in the front-back direction. Then, the AC voltage generator applies an AC voltage at the same frequency between the second pair of transducers for a second interval of time (e.g., one second), which generates an electric field with field lines that generally run in the right-left direction. The system then repeats this two-step sequence for the duration of the treatment.

BRIEF DESCRIPTION OF THE DRAWINGS

Various embodiments are described in detail below with reference to the accompanying drawings, wherein like reference numerals represent like elements.

DESCRIPTION OF THE INVENTION

Figures 1A, 1B:
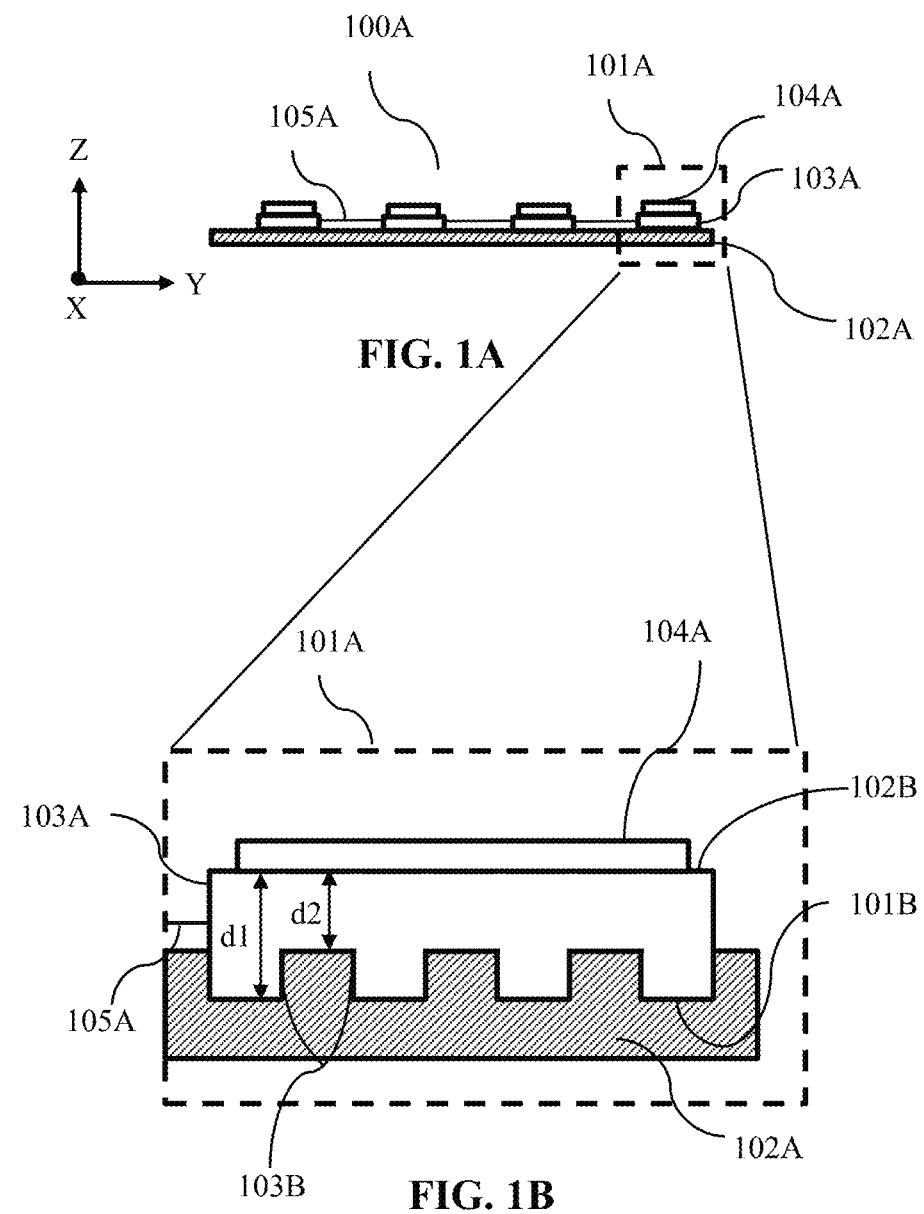
FIG. 1A is a cross-sectional diagram of an exemplary embodiment of a transducer with a plurality of coupled electrode elements for delivering tumor treating fields to a subject's body.
FIG. 1B depicts an enlarged cross-sectional view of one of the electrode elements in FIG. 1A.

The present invention can be understood more readily by reference to the following detailed description, examples, drawings, and claims, and their previous and following description. However, it is to be understood that this invention is not limited to the specific apparatuses, devices, systems, and/or methods disclosed unless otherwise specified, and as such, of course, can vary.

Headings are provided for convenience only and are not to be construed to limit the invention in any manner. Embodiments illustrated under any heading or in any portion of the disclosure may be combined with embodiments illustrated under the same or any other heading or other portion of the disclosure.

Any combination of the elements described herein in all possible variations thereof is encompassed by the invention unless otherwise indicated herein or otherwise clearly contradicted by context.

Unless otherwise expressly stated, it is in no way intended that any method or aspect set forth herein be construed as requiring that its steps be performed in a specific order. Accordingly, where a method claim does not specifically state in the claims or description that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of embodiments described in the specification. It is to be understood that both the foregoing general description and the following detailed description are exemplary and explanatory only and are not restrictive.

In this specification and in the claims which follow, reference will be made to a number of terms which are defined herein.

As used in the specification and the appended claims, the singular forms "a," "an" and "the" include plural referents unless the context clearly dictates otherwise.

As used herein, the terms "optional" or "optionally" mean that the subsequently described event, condition, component, or circumstance may or may not occur, and that the description includes instances where said event, condition, component, or circumstance occurs and instances where it does not.

As used herein, the term "protrusion" refers to a portion of a surface that extends or protrudes outward from surrounding portions of the surface, including but not limited to a bump, a ridge, or a wrinkle. As used herein, the term "indentation" refers to a portion of a surface that extends inward or is recessed relative to surrounding portions of the surface, including but not limited to a dent, a divot, a groove, or a wrinkle. As used herein, the term "protrusions or indentations" includes "protrusions and/or indentations."

In applying an AC voltage to the body, some voltage is wasted by way of a voltage drop across the dielectric layer of the electrode elements in the transducers. Therefore, there is a need for a system (apparatus) or method that can deliver the maximum voltage to the body without altering the footprint of the transducers, since there is a limit to the area that can be used for attachment of the transducer arrays on the desired location of the body. The present invention provides a solution to this problem as well as addressing other important issues.

When delivering tumor treating fields (TTFields) to the subject's body, an AC voltage with low intensity (e.g., 1-4 V/cm) and intermediate frequency (e.g., 50-500 kHz) is applied between transducers, e.g., capacitors. As described herein, the transducers comprise electrode elements, which in turn typically comprise a dielectric layer sandwiched between conductive layers. The latter arrangement functions as a capacitor. Capacitance (C) characterizes the amount of charge (Q) stored per unit voltage (V) between the conductors. Capacitance is inversely proportional to impedance, so a high capacitance translates to a low impedance and correspondingly low voltage drop on the transducer arrays.

The inventors discovered an approach to increase the capacitance of the transducers by using transducers comprising electrode elements having a dielectric layer with a non-planar surface. With a non-planar surface, the distance between the two surfaces of the dielectric layer becomes nonuniform, and thus the capacitance of the transducer is changed. As described herein, this may improve the electric field power to be delivered to the subject's body for treating a tumor, and thus the efficiency of TTFields treatment may be improved.

FIG. 1A depicts a cross-sectional view of an exemplary embodiment of a transducer with a plurality of coupled electrode elements for delivering tumor treating fields to a subject's body. In this example, a plurality of electrode elements 101A is integrated into a transducer 100A.

With reference to FIG. 1A, the electrode element 101A may comprise a substrate 102A. The substrate 102A is configured for contact with a subject's body or attaching the transducer 100A to a subject's body for delivering TTFields. Suitable materials for the substrate 102A should be, or contain, conductive materials and may include, for example, cloth, foam, and flexible plastic. In one example, the substrate 102A is or includes a conductive medical gel which may typically have a thickness of approximately 0.5 mm or more, or may be infused/absorbed in the substrate material (cloth, foam, flexible plastic, etc.). In a more specific example, the substrate 102A is a layer of conductive hydrogel with a minimum thickness of 0.5 mm. In another example, the substrate 102A is or includes a conductive adhesive which may typically have a thickness of approximately 20 µm or more, or may be infused/absorbed in the substrate material (cloth, foam, flexible plastic, etc.).

The plurality of electrode elements 101A may be connected to one another through conductive wires 105A. In this example, the plurality of electrode elements 101A are mechanically and electrically connected to one another through the conductive wires 105A. In a different example, the plurality of electrode elements 101A are connected to one another through conductive wires without a substrate 102A.

In one embodiment, at least one of the plurality of electrode elements 101A comprises a dielectric layer 103A. In one embodiment, the dielectric layer 103A has a first surface facing the subject's body and a second surface opposite the first surface. In the example depicted in FIG. 1A, the first surface of the dielectric layer 103A is the surface in direct contact with the substrate 102A. In one example, the first surface is a non-planar surface and the second surface is substantially planar surface.

In one embodiment, the dielectric layer 103A is a ceramic layer. In one example, the dielectric layer 103A is a circular ceramic disk. In another example, the dielectric layer 103A is a ceramic element that is not circular shaped or disk-shaped. In another example, the dielectric layer 103A is a non-ceramic dielectric material. Examples of a non-ceramic dielectric material include polymer films or polymer layers.

In alternative embodiments, the transducer 100A may include only one single electrode element. In one example, the single electrode element may be a flexible organic material or flexible organic composite positioned on a substrate. In another example, the electrode element may include a flexible organic material or flexible organic composite without a substrate.

The electrode element 101A may further comprise a conductive layer 104A. In the example depicted in FIG. 1A, the conductive layer 104A is in direct contact with the second surface of the dielectric layer 103A. In one example, the conductive layer 104A is a metal layer.

Other alternative constructions for implementing the transducer for use with embodiments of the invention may also be used, as long as they are capable of (a) delivering TTFields to the subject's body and (b) being positioned at locations of the subject's body. In other embodiments, any electric field generating device may be used with the embodiments of the invention as long as the electric field generating device is capable of delivering TTFields to the subject's body.

FIG. 1B depicts an example of an enlarged cross-sectional view of the electrode element 101A in FIG. 1A. In one embodiment, the electrode element 101A comprises a substrate 102A, a dielectric layer 103A, and a conductive layer 104A. In one embodiment, the dielectric layer 103A has a first surface 101B facing the subject's body and a second surface 102B opposite the first surface. In this example, the first surface 101B is in direct contact with the substrate 102A, and the second surface 102B is in direct contact with the conductive layer 104A.

In one embodiment, the first surface 101B is a non-planar surface, and the second surface 102B is a substantially planar surface. In one example, the first surface 101B is a nonuniform surface or an uneven surface. As a result, the thickness of the dielectric layer 103A is nonuniform or uneven. The first surface 101B may also be nonuniform or uneven. As an example, the non-planar first surface 101B is a surface with at least one protrusion or indentation, such as, for example, a bump, dent, divot, ridge, groove, or wrinkle, or the like, or combination thereof. In one example, the non-planar first surface 101B is a surface with protrusions and indentations. In one example, the non-planar first surface 101B is a chemically etched surface with at least one protrusion or indentation. In another example, the non-planar first surface 101B is cut using a cutting tool, a laser, or a water jet. In another example, the non-planar first surface 101B is imprinted or molded.

In another embodiment, the non-planar first surface 101B is a surface with a plurality of sidewalls 103B. In one example, the plurality of sidewalls 103B is the sides of at least one protrusion or indentation of the non-planar first surface 101B. In one example, the plurality of sidewalls 103B, when viewed from a cross-sectional direction, comprise at least two substantially vertical sidewalls, at least two curved or rounded sidewalls, at least two inclined sidewalls, at least two stepped sidewalls, or a mix thereof. Examples of these embodiments are further illustrated in FIGS. 2A-2F, which are discussed further below.

In another embodiment, when viewed from a direction perpendicular to the first surface, the protrusions or indentations of the non-planar surface 101B are arranged as a pattern. As an example, when viewed from a direction perpendicular to the first surface, the protrusions or indentations of the non-planar first surface 101B are arranged as at least two substantially parallel lines, at least two substantially perpendicular lines, at least two substantially concentric circles, at least two substantially similarly sized circles, or at least two substantially similar square or rectangular shapes, or a combination thereof. In another embodiment, when viewed from a direction perpendicular to the first surface, the protrusions or indentations of the non-planar surface 101B are arranged in a random manner. Examples of these embodiments are further illustrated in FIGS. 3A-3E, which are discussed further below.

In another embodiment, the distance between the first surface 101B and the second surface 102B of the dielectric layer 103A is nonuniform. In the example depicted in FIG. 1B, the distance between the first surface 101B and the second surface 102B includes: a first distance $d_1$ between the top of the protrusion and the second surface 102B; and a second distance $d_2$ between the bottom of the protrusion of the first surface 101B and the second surface 102B. In this example, $d_2$ is smaller than $d_1$. In one example, the difference between $d_1$ and $d_2$ is less than or equal to 30% of $d_1$. In another example, the difference between $d_1$ and $d_2$ is less than or equal to 20% of $d_1$, or less than or equal to 10% of $d_1$.

Maximizing the voltage delivered to the body may be achieved by minimizing the voltage wasted by way of a voltage drop across the dielectric layer of the electrode elements in the transducers. Due to the inverse nature of voltage and capacitance in a capacitor, the latter (minimizing the voltage drop) can be achieved by maximizing the capacitance in the electrode elements of the transducers.

Generally speaking, the capacitance of the dielectric layer may be calculated by the following equation:

$$C = \epsilon A/d \quad \text{Equation 1}$$

where $\epsilon$ is the absolute permittivity of the dielectric material; A is the surface areas of the two parallel surfaces of the dielectric layer; and d is the distance between the two surfaces of the dielectric layer.

Assuming the surface area and absolute permittivity of the dielectric layer remain constant, a reduction in the distance d between the conductive layers (i.e. reduction in the thickness of the dielectric layer) would increase the capacitance. In FIG. 1B, a reduction of the whole layer thickness from $d_1$ to $d_2$ would increase the capacitance. At the lower limit of thickness, $d_2$, the dielectric layer may be too fragile and lack the durability for the intended use, but at the larger thickness, $d_1$, the durability may be improved and may be sufficient for use. FIG. 1B illustrates the use of protrusions in the dielectric layer 103A to increase the layer thickness in the area of the protrusions to the larger thickness $d_1$ to recover some aspect of the durability of the thicker dielectric layer. For the simplified step protrusion/indentation of FIG. 1B having just two distances (dielectric layer thicknesses) $d_1$ and $d_2$, the sum of all area (observed perpendicular to the X-Y plane) with distance $d_1$ is $A_1$, and the sum of all area (observed perpendicular to the X-Y plane) with distance $d_2$ is $A_2$. The total capacitance, $C_{total} = C_1 + C_2$, where:

$$C_1 = \epsilon A_1/d_1 \text{ and}$$

$$C_2 = \epsilon A_2/d_2$$

Therefore, the capacitance of the representative area fraction of the dielectric layer with the smaller thickness (distance $d_2$) is larger than the representative area fraction of the dielectric layer with distance $d_1$ (because the capacitance is inversely related to the distance (dielectric thickness)). As such, by having a non-planar first surface, the overall capacitance of the dielectric layer is increased compared to that for a dielectric layer having a thickness $d_1$. Moreover, the improvement in capacitance is further boosted because the capacitance is proportional to the surface area of the dielectric layer, which is greatly increased by the inclusion of the protrusions/indentations in the surface of the dielectric layer (the surface area is increased, for example, by the additional sidewalls of the indentations and raised surfaces of the raised protrusions).

FIGS. 2A-2F depict cross-sectional diagrams of exemplary embodiments of the structure of a dielectric layer with a non-planar surface.

Figure 2A:
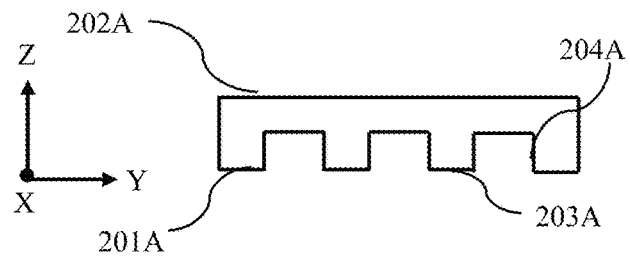
FIGS. 2A-2F depict cross-sectional diagrams of exemplary embodiments of the structure of dielectric layer with a non-planar surface.

FIG. 2A depicts an example of the structure of the dielectric layer. In this example, the dielectric layer has a first non-planar surface 201A and a second substantially planar surface 202A. In one embodiment, the first non-planar surface 201A has one or more protrusions (bumps) 203A. In one example, the one or more protrusions 203A has at least two vertical sidewalls 204A. The term "vertical" refers to a direction that is perpendicular or approximately perpendicular (e.g., within +/−10 degrees of perpendicular) to the first surface.

Figure 2B:
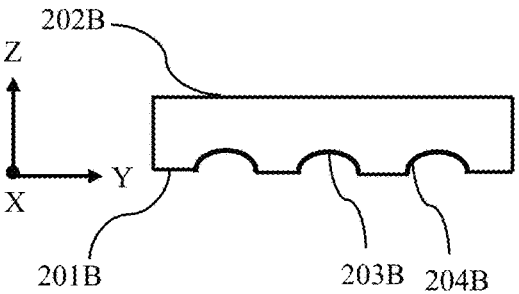

FIG. 2B depicts another example of the structure of the dielectric layer. In this example, the dielectric layer has a first non-planar surface 201B and a second substantially planar surface 202B. In one embodiment, the first non-planar surface 201B has one or more substantially rounded indentations 203B. In one example, the one or more substantially rounded indentations 203B has at least two curved sidewalls 204B.

Figure 2C:
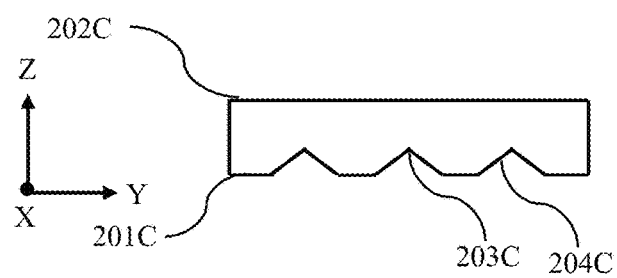

FIG. 2C depicts another example of the structure of the dielectric layer. In this example, the dielectric layer has a first non-planar surface 201C and a second substantially planar surface 202C. In one embodiment, the first non-planar surface 201C has one or more substantially triangular indentations (grooves) 203C. In one example, the one or more substantially triangular indentations 203C has two inclined sidewalls 204C.

Figure 2D:
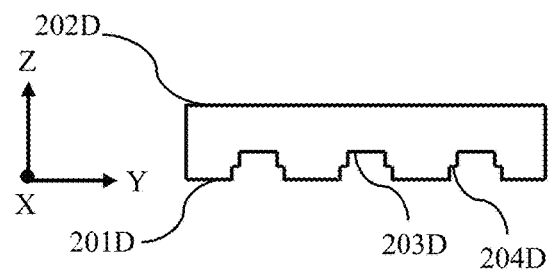

FIG. 2D depicts another example of the structure of the dielectric layer. In this example, the dielectric layer has a first non-planar surface 201D and a second substantially planar surface 202D. In one embodiment, the first non-planar surface 201D has one or more indentations 203D. In one example, the one or more indentations 203C has at least two stepped sidewalls 204D.

Figure 2E:
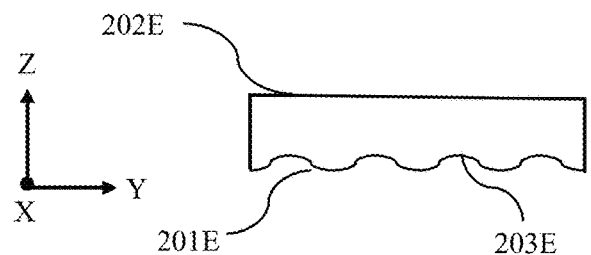

FIG. 2E depicts another example of the structure of the dielectric layer. In this example, the dielectric layer has a first non-planar surface 201E and a second substantially planar surface 202E. In one embodiment, the first non-planar surface 201E has one or more alternating protrusions-indentations (wrinkles) 203E.

Figure 2F:
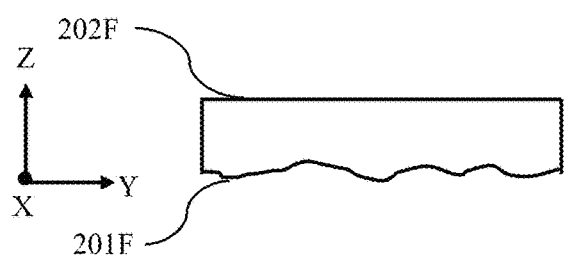

FIG. 2F depicts another example of the structure of the dielectric layer. In this example, the dielectric layer has a first non-planar surface 201F and a second substantially planar surface 202F. In one embodiment, the first non-planar surface 201F has a random surface structure of protrusions and indentations, such as valleys, peaks, inclines, curves, walls, etc.

It is to be understood that the embodiments described herein are not to be considered as limiting, as clearly other protrusions/indentations are possible. Further, embodiments exist for which the second surface is non-planar, either in addition to, or instead of, the first non-planar surface, and such protrusions/indentations may be present on the second surface in these embodiments.

FIGS. 3A-3E depict examples of the appearance of the non-planar first surface of the dielectric layer when viewed from a direction perpendicular to the non-planar surface. In FIGS. 3A-3E, when viewed from a direction perpendicular to the first surface, the protrusions and indentations of the non-planar first surface are arranged as a pattern. However, it should be noted that in some other embodiments, when viewed from a direction perpendicular to the first surface, the protrusions and indentations of the non-planar first surface may be arranged in a random manner.

Figure 3A:
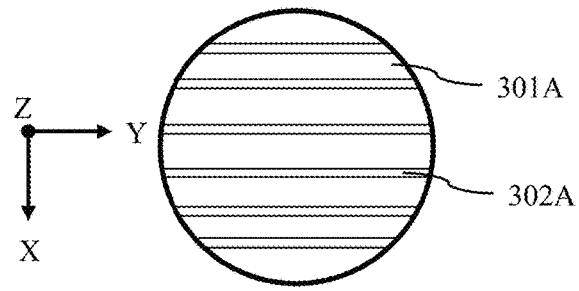
FIGS. 3A-3E depict top views of exemplary embodiments of the appearance of dielectric layer with a non-planar surface when viewed from a direction perpendicular to the non-planar surface.

FIG. 3A depicts an example of the appearance of the non-planar first surface. In this example, the first non-planar surface 301A illustrates protrusions and/or indentations of the non-planar first surface as at least two substantially parallel lines 302A.

Figure 3B:
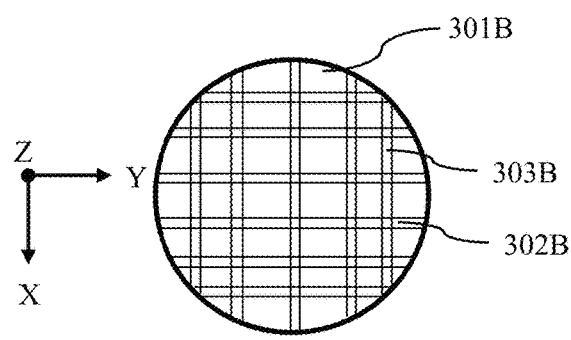

FIG. 3B depicts another example of the appearance of the non-planar first surface. In this example, the first non-planar surface 301B illustrates protrusions and/or indentations of the non-planar first surface as at least two substantially perpendicular lines 302B and 303B.

Figure 3C:
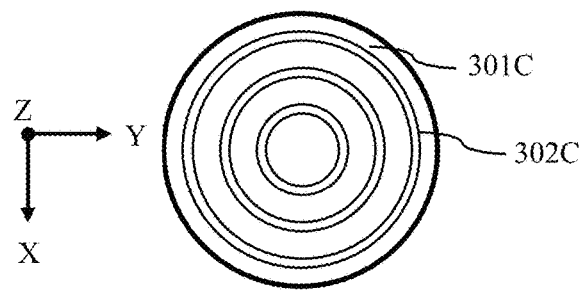

FIG. 3C depicts another example of the appearance of the non-planar first surface. In this example, the first non-planar surface 301C illustrates protrusions and/or indentations of the non-planar first surface as at least two substantially concentric circles 302C.

Figure 3D:
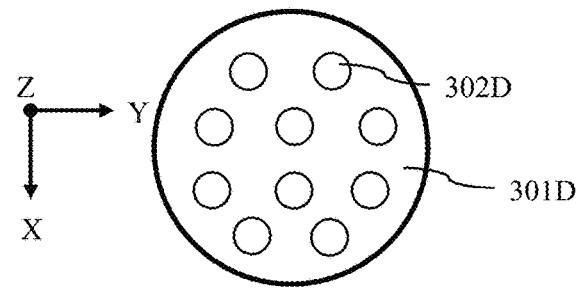

FIG. 3D depicts another example of the appearance of the non-planar first surface. In this example, the first non-planar surface 301D illustrates protrusions and/or indentations of the non-planar first surface as at least two substantially similarly sized circles 302D.

Figure 3E:
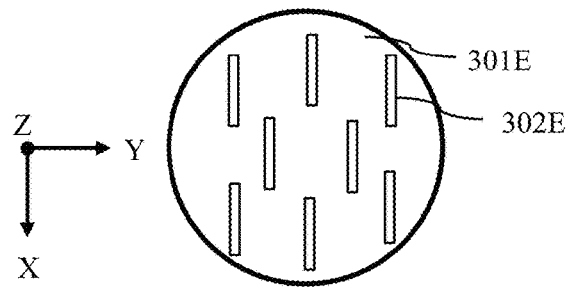

FIG. 3E depicts another example of the appearance of the non-planar first surface. In this example, the first non-planar surface 301E illustrates protrusions and/or indentations of the non-planar first surface as at least two substantially similarly sized rod-shaped rectangles 302E. In other embodiments, the protrusions and/or indentations of the non-planar first surface may be at least two substantially similarly sized squares or other polygon shapes.

Figure 4A:
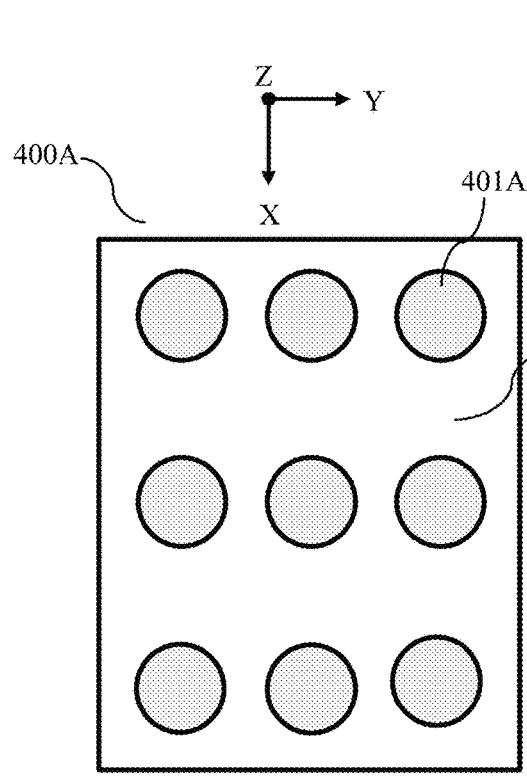
FIGS. 4A and 4B depict top views of exemplary embodiments of the structure of transducers with a plurality of coupled electrode elements.
Figure 4B:
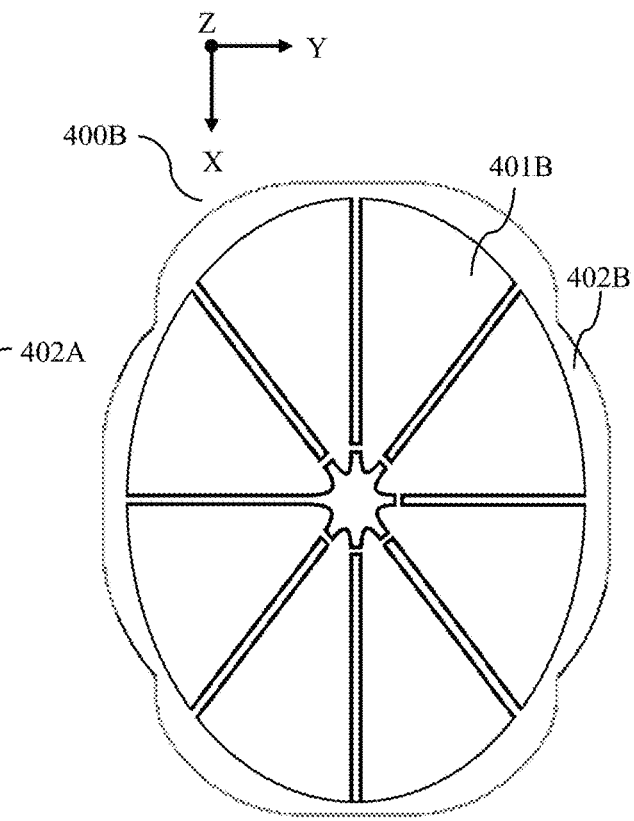

FIGS. 4A and 4B depict top views of exemplary embodiments of the structure of a transducer with a plurality of coupled electrode elements. For example, as shown in FIG. 4A, the transducer 400A has a substrate 402A and a plurality of electrode elements 401A. The substrate 402A is configured for attaching the transducer to a subject's body. Suitable materials for the substrate 402A include, for example, cloth, foam, and flexible plastic. In some embodiments, the substrate 402A includes a conductive medical gel having a thickness of not less than approximately 0.5 mm, or a conductive adhesive having a thickness of not less than 20 µm. In a more specific example, the substrate 402A is a layer of hydrogel with a minimum thickness of approximately 0.5 mm. In this situation, the transducer 400A is attached to the subject's body through the substrate 402A.

A plurality of capacitively coupled electrode elements 401A are positioned on the substrate 402A, and each of the capacitively coupled electrode elements has a conductive plate with a dielectric layer disposed thereon that faces towards the substrate. In one embodiment, the dielectric layer has a first surface facing the subject's body and a second surface opposite the first surface. In one example, the dielectric layer has a first surface in contact with the substrate and a second surface in contact with the conductive plate. In some examples, at least one of the plurality of electrode elements has a dielectric layer with a non-planar surface. For example, the non-planar surface may be the first surface of the dielectric layer. Optionally, one or more sensors may be positioned beneath each of the electrode elements in a manner that is similar to the conventional arrangement used in the Novocure Optune® system. In one example, the one or more sensors are temperature sensors (e.g., thermistors).

In some embodiments, the plurality of electrode elements 401A are substantially flat electrode elements. In one example, the dielectric layer of the electrode elements is a circular dielectric layer. In a more specific example, the dielectric layer is a ceramic disk, and each of the ceramic disks is approximately 2 cm in diameter and approximately 1 mm in thickness at the largest thickness. In other embodiments, the dielectric layer is a non-circular dielectric layer. In other embodiments, the dielectric layer is a ceramic element that is not disk-shaped.

FIG. 4B depicts an example of the transducer 400B with non-ceramic coupled electrode elements 401B. In this example, the transducer 400B has a substrate 402B and a plurality of electrode elements 401B each of which comprises a non-ceramic dielectric layer. In one embodiment, the non-ceramic dielectric layer includes a flexible dielectric material. Examples of flexible dielectric materials include dielectric polymers or dielectric co-polymers. In some embodiments, the non-ceramic dielectric layer 401B is non-circular shaped. In FIG. 4B, the electrode elements 401B (and the polymer dielectric layer) are substantially triangle or wedge shaped, although in other embodiments, the non-ceramic dielectric layer (e.g., polymer layer) may be any shape. In some examples, the non-ceramic dielectric layer is approximately 1 mm, or less, in thickness at the largest thickness. In another embodiment, the transducer 400B does not include a substrate. In such an embodiment, the non-ceramic dielectric layer may be directly attached to the subject's body, optionally via a layer of hydrogel or conductive adhesive.

The dielectric layer may have a first surface facing the subject's body and a second surface opposite the first surface. In one example, the dielectric layer has a first surface in contact with the substrate and a second surface in contact with a conductive material. In some embodiments, at least one of the plurality of electrode elements has a dielectric layer with at least one non-planar surface. In some embodiments, at least one of the plurality of electrode elements has a dielectric layer with a non-planar first surface.

Transducers that use an array of electrode elements that are not capacitively coupled may also be used. In this situation, the transducers 400A and 400B may be implemented using a region of a conductive material that is configured for placement against a subject's body, with no insulating dielectric layer disposed between the conductive element and the body.

Figure 5A:
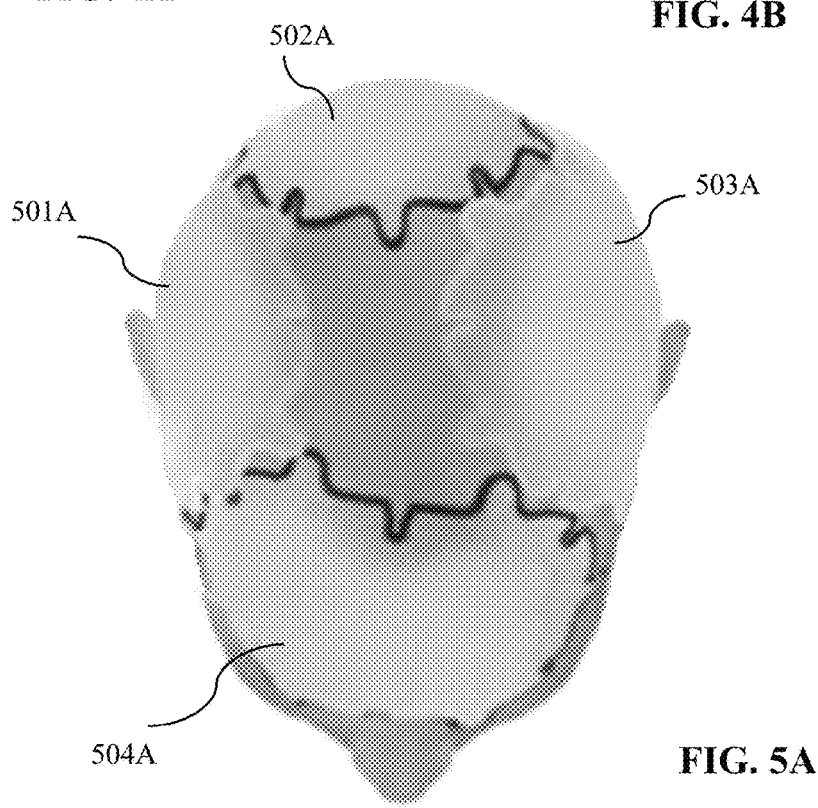
FIGS. 5A and 5B depict exemplary embodiments for attaching transducers to the subject's body for delivering tumor treating fields.
Figure 5B:
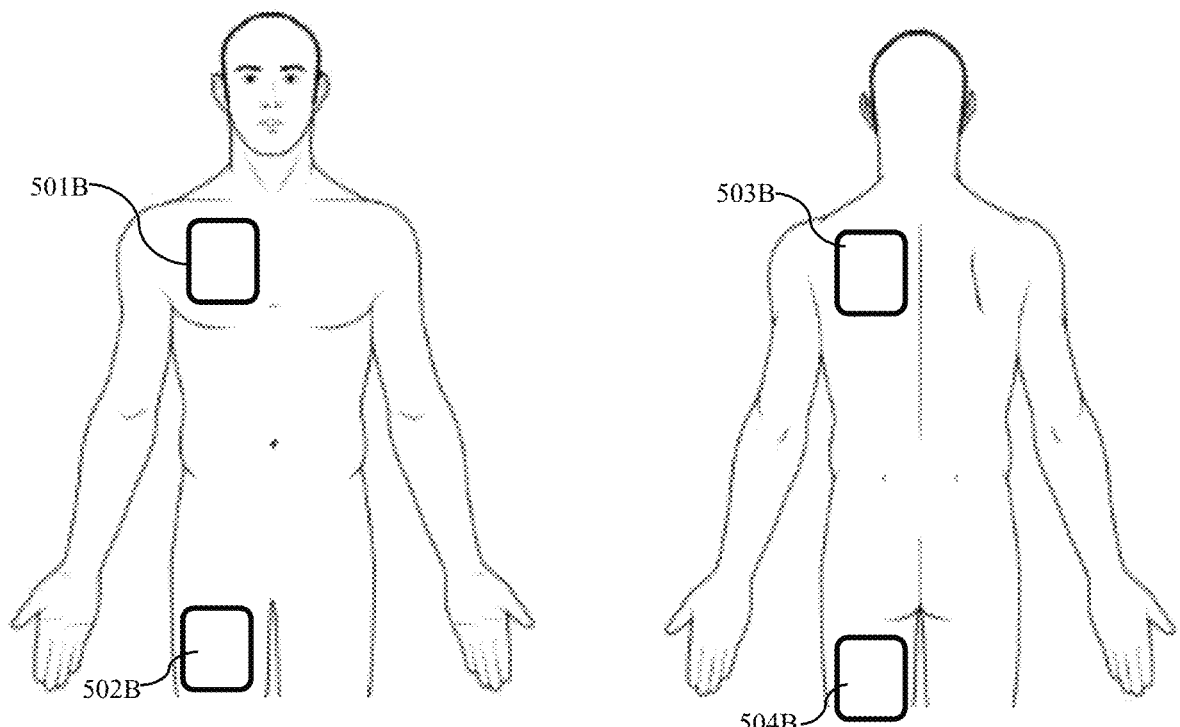

FIGS. 5A and 5B depict exemplary embodiments of attaching the transducers to the subject's body for delivering tumor treating fields.

In the example depicted in FIG. 5A, transducers 501A, 502A, 503A, and 504A are attached to a subject's head for applying TTFields to the subject's head. In one embodiment, two electric fields are alternately applied between two pairs of transducers. Each pair of transducers corresponds to a channel for generating TTFields in the subject's body. As for pairs of transducers, the transducer 501A and 503A may form a first pair of transducers and the transducer 502A and 504A may form a second pair of transducers.

In this example, a first tumor treating electric field (TT-Field) between the first pair of transducers and a second tumor treating electric field (TTField) between the second pair of transducers are alternately generated. The first TTField is produced by applying a first AC voltage generated by a first AC generator between the first pair of transducers for a first time period and has, for example, a low intensity (e.g., 1-4 V/cm) and intermediate frequency range (e.g., 50-576 kHz, or in some cases, 125-250 kHz). In one example, the frequency of the first TTField is 150 kHz. The first AC voltage is applied to the first pair of transducers for the first time period (e.g., one second). After the first time period, the generation of the first TTField is ceased. Next, the second TTField is produced by applying a second AC voltage generated by a second AC generator between the second pair of transducers for a second time period and has, for example, a low intensity (e.g., 1-4 V/cm) and intermediate frequency range (e.g., 50-576 kHz, or in some cases, 125-250 kHz). In one example, the frequency of the second TTField is 150 kHz. The second AC voltage is applied to the second pair of transducers for the second time period (e.g., one second). The second time period and the first time period may be the same or different. After the second time period, the generation of the second TTField is ceased. Next, the method repeats the process of alternately generating the first TTFields between the first pair of transducers for the first time period and generating the second TTFields between the second pair of transducers for the second time period.

In the example depicted in FIG. 5B, transducers 501B, 502B, 503B, and 504B are attached to a subject's body for applying TTFields to the subject's torso. In one embodiment, two electric fields are alternately applied between two pairs of transducers. Each pair of transducers corresponds to a channel for generating TTFields in the subject's body. In the example depicted in FIG. 5B, transducer 501B is attached to the front of the subject's right chest, transducer 502B is attached to the front of subject's right thigh, transducer 503B is attached to the back of the subject's left chest, and transducer 504B is attached to the back of the subject's left thigh. As for pairs of transducers, the transducers 501B and 504B may form a first pair of transducers, and the transducers 502B and 503B may form a second pair of transducers.

Figure 6:
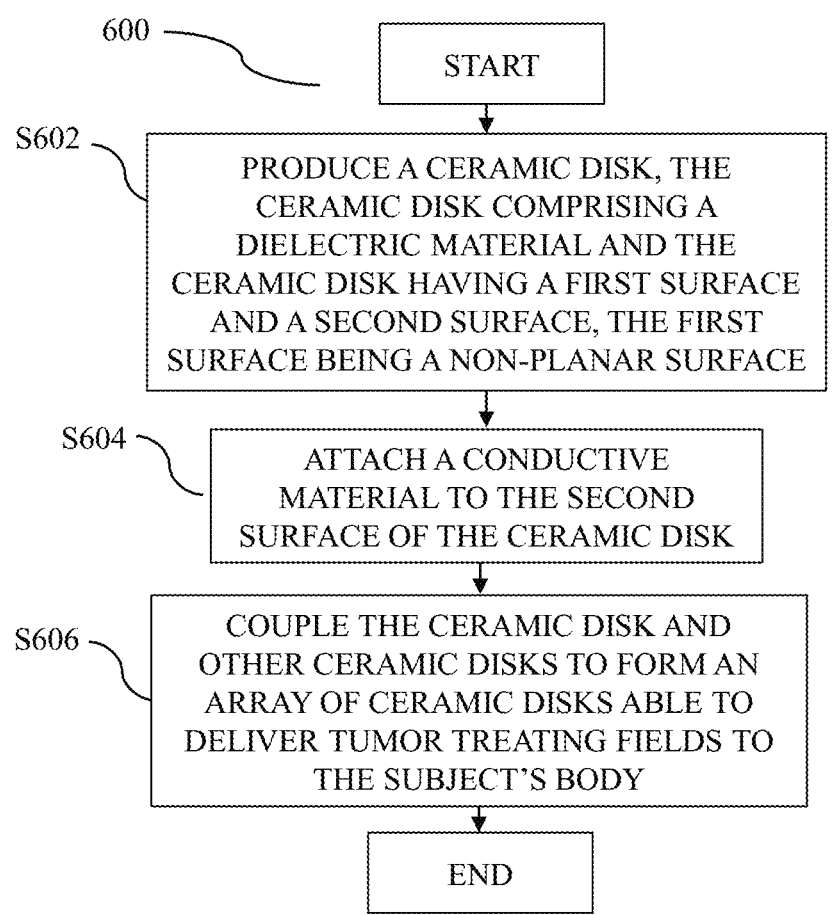
FIG. 6 is a process flow diagram depicting an exemplary embodiment of a process to manufacture an apparatus for delivering tumor treating fields to the subject's body.

FIG. 6 is a process flow diagram depicting an exemplary embodiment of a process to manufacture an apparatus for delivering tumor treating fields to the subject's body.

With reference to FIG. 6, at step S602, the method comprises producing a ceramic disk. In some embodiments, the ceramic disk comprises a dielectric material. The ceramic disk has a first surface and a second surface, and the first surface is a non-planar surface. In one embodiment, the method further comprises chemical etching or cutting the first surface of the ceramic disk to produce the non-planar surface. In some examples, the first surface of the ceramic disk is cut using a cutting tool, a laser, or a water jet. In other embodiments, the method comprises imprinting or molding the first surface of the ceramic disk to produce the non-planar surface.

At step S604, the method comprises attaching a conductive material to the second surface of the ceramic disk. In some embodiments, the second surface of the ceramic disk is substantially planar. In one example, the conductive material is metal. In a more specific example, the conductive material is a metal layer.

At step S606, the method comprises coupling the ceramic disk and other ceramic disks to form an array of ceramic disks able to deliver TTFields to the subject's body. In some embodiments, one or more of the other ceramic disks have a non-planar first surface. In other embodiments, one or more of the other ceramic disks have two substantially planar surfaces.

FIG. 6 discusses a method of manufacturing an array of ceramic disks according to an embodiment of the invention. In other embodiments of the invention, similar methods of manufacturing may be used to produce an array of electrodes comprising polymer films. To obtain one or more non-planar surface on the polymer films, the surface of the polymer films may be imprinted or molded. For example, the first surface of the polymer films may be imprinted or molded.

Illustrative Embodiments

The invention includes other illustrative embodiments, such as the following.

Illustrative Embodiment 1. An apparatus for delivering tumor treating fields to a subject's body, the apparatus comprising: a plurality of electrically coupled electrode elements to be located on a subject's body and able to deliver tumor treating fields to the subject's body, wherein at least one electrode element of the plurality of electrically coupled electrode elements comprises a dielectric layer, the dielectric layer has a first surface to face the subject's body and a second surface opposite the first surface, and at least one of the first surface and the second surface of the dielectric layer is a non-planar surface.

Illustrative Embodiment 2. The apparatus of Illustrative Embodiment 1, wherein the first surface of the dielectric layer is non-planar and the second surface of the dielectric layer is substantially planar.

Illustrative Embodiment 3. The apparatus of Illustrative Embodiment 2, wherein the non-planar first surface is a surface with at least one protrusion or indentation.

Illustrative Embodiment 4. The apparatus of Illustrative Embodiment 3, wherein the non-planar first surface is a chemically etched surface with at least one protrusion or indentation.

Illustrative Embodiment 5. The apparatus of Illustrative Embodiment 3, wherein, when viewed from a direction perpendicular to the first surface, the protrusions or indentations of the non-planar first surface are arranged as a pattern.

Illustrative Embodiment 6. The apparatus of Illustrative Embodiment 3, wherein, when viewed from a direction perpendicular to the first surface, the protrusions or indentations of the non-planar first surface are arranged as at least two substantially parallel lines, at least two substantially perpendicular lines, at least two substantially concentric circles, at least two substantially similarly sized circles, or at least two substantially square or rectangular shapes, or a combination thereof.

Illustrative Embodiment 7. The apparatus of Illustrative Embodiment 3, wherein, when viewed from a direction perpendicular to the first surface, the protrusions or indentations of the non-planar first surface are arranged in a random manner.

Illustrative Embodiment 8. The apparatus of Illustrative Embodiment 2, wherein the non-planar first surface is a surface with a plurality of sidewalls and wherein the plurality of sidewalls comprises at least two vertical sidewalls, at least two curved sidewalls, at least two inclined sidewalls, at least two stepped sidewalls, or a combination thereof.

Illustrative Embodiment 9. The apparatus of Illustrative Embodiment 2, wherein the at least one electrode element comprises a circular ceramic disk.

Illustrative Embodiment 10. The apparatus of Illustrative Embodiment 2, wherein the at least one electrode element comprises a polymer film or polymer layer.

Illustrative Embodiment 11. The apparatus of Illustrative Embodiment 2, wherein the at least one electrode element is non-circular shaped.

Illustrative Embodiment 12. The apparatus of Illustrative Embodiment 2, wherein the at least one electrode element further comprises: a substrate in direct contact with the first surface of the dielectric layer; and a conductive layer in direct contact with the second surface of the dielectric layer.

Illustrative Embodiment 13. The apparatus of Illustrative Embodiment 12, wherein the substrate is in contact with or attaches to the subject's body when delivering tumor treating fields.

Illustrative Embodiment 14. The apparatus of Illustrative Embodiment 2, wherein the at least one electrode element further comprises hydrogel or a conductive adhesive on the first surface of the dielectric layer.

Illustrative Embodiment 15. The apparatus of Illustrative Embodiment 2, wherein the at least one electrode element further comprises a metal layer on the second surface of the dielectric layer.

Illustrative Embodiment 16. The apparatus of Illustrative Embodiment 1, wherein the first surface of the dielectric layer is non-planar, the second surface of the dielectric layer is substantially planar, and wherein a distance between the non-planar first surface and the substantially planar second surface is nonuniform and varies by less than or equal to 30%.

Illustrative Embodiment 17. The apparatus of Illustrative Embodiment 1, wherein the electrode elements are capacitively coupled.

Illustrative Embodiment 18. The apparatus of Illustrative Embodiment 1, wherein the electrode elements are not capacitively coupled.

Illustrative Embodiment 19. An apparatus for delivering tumor treating fields to a subject's body, the apparatus comprising: an array of connected electrode elements to be located on a subject's body and able to deliver tumor treating fields to the subject's body, wherein at least one electrode element of the array comprises a ceramic disk, wherein the ceramic disk has a first surface to face the subject's body and a second surface opposite the first surface, and wherein the ceramic disk has a nonuniform thickness.

Illustrative Embodiment 20. The apparatus of Illustrative Embodiment 19, wherein, when viewed in cross-section, the first surface of the ceramic disk has a nonuniform surface.

Illustrative Embodiment 21. The apparatus of Illustrative Embodiment 19, wherein, when viewed in cross-section, the first surface of the ceramic disk has an uneven surface.

Illustrative Embodiment 22. An apparatus for delivering tumor treating fields to a subject's body, the apparatus comprising: a transducer to be located on a subject's body and able to deliver tumor treating fields to the subject's body, wherein the transducer comprises one or more electrode elements having a first surface to face the subject's body and a second surface opposite the first surface, and wherein at least one of the electrode elements comprises a polymer film having a first surface to face the subject's body and a second surface opposite the first surface, and wherein the polymer film has a nonuniform thickness.

Illustrative Embodiment 23. The apparatus of Illustrative Embodiment 22, wherein, when viewed in cross-section, the first surface of the polymer film has a nonuniform surface.

Illustrative Embodiment 24. The apparatus of Illustrative Embodiment 22, wherein, when viewed in cross-section, the first surface of the polymer film has an uneven surface.

Illustrative Embodiment 25. A method of manufacturing an apparatus for delivering tumor treating fields to a subject's body, the method comprising: producing a ceramic disk, the ceramic disk comprising a dielectric material able to deliver tumor treating fields to the subject's body, the ceramic disk having a first surface to face the subject's body and a second surface opposite the first surface, the first surface of the ceramic disk being a non-planar surface; attaching a conductive material to the second surface of the ceramic disk; and coupling the ceramic disk and other ceramic disks to form an array of ceramic disks able to deliver tumor treating fields to the subject's body.

Illustrative Embodiment 26. The method of Illustrative Embodiment 25, further comprising chemical etching or cutting the first surface of the ceramic disk to produce the non-planar surface.

Illustrative Embodiment 27. The method of Illustrative Embodiment 25, wherein the first surface of the ceramic disk is cut using a cutting tool, a laser, or a water jet.

While the present invention has been disclosed with reference to certain embodiments, numerous modifications, alterations, and changes to the described embodiments are possible without departing from the sphere and scope of the present invention, as defined in the appended claims. Accordingly, it is intended that the present invention not be limited to the described embodiments, but that it has the full scope defined by the language of the following claims, and equivalents thereof.

What is claimed is:

1. An apparatus for delivering tumor treating fields to a subject's body, the apparatus comprising:
    a plurality of electrically coupled electrode elements to be located on a subject's body and able to deliver tumor treating fields to the subject's body,
    wherein at least one electrode element of the plurality of electrically coupled electrode elements comprises a dielectric layer, the dielectric layer has a first surface to face the subject's body and a second surface opposite the first surface, and at least one of the first surface and the second surface of the dielectric layer is a non-planar surface.

2. The apparatus of claim 1, wherein the first surface of the dielectric layer is non-planar and the second surface of the dielectric layer is substantially planar.

3. The apparatus of claim 2, wherein the non-planar first surface is a surface with at least one protrusion or indentation.

4. The apparatus of claim 3, wherein the non-planar first surface is a chemically etched surface with at least one protrusion or indentation.

5. The apparatus of claim 3, wherein, when viewed from a direction perpendicular to the first surface, the protrusions or indentations of the non-planar first surface are arranged as a pattern.

6. The apparatus of claim 3, wherein, when viewed from a direction perpendicular to the first surface, the protrusions or indentations of the non-planar first surface are arranged as at least two substantially parallel lines, at least two substantially perpendicular lines, at least two substantially concentric circles, at least two substantially similarly sized circles, or at least two substantially square or rectangular shapes, or a combination thereof.

7. The apparatus of claim 3, wherein, when viewed from a direction perpendicular to the first surface, the protrusions or indentations of the non-planar first surface are arranged in a random manner.

8. The apparatus of claim 2, wherein the non-planar first surface is a surface with a plurality of sidewalls and wherein the plurality of sidewalls comprises at least two vertical sidewalls, at least two curved sidewalls, at least two inclined sidewalls, at least two stepped sidewalls, or a combination thereof.

9. The apparatus of claim 2, wherein the at least one electrode element comprises a circular ceramic disk.

10. The apparatus of claim 2, wherein the at least one electrode element comprises a polymer film or polymer layer.

11. The apparatus of claim 2, wherein the at least one electrode element is non-circular shaped.

12. The apparatus of claim 2, wherein the at least one electrode element further comprises:
    a substrate in direct contact with the first surface of the dielectric layer; and
    a conductive layer in direct contact with the second surface of the dielectric layer.

13. The apparatus of claim 12, wherein the substrate is in contact with or attaches to the subject's body when delivering tumor treating fields.

14. The apparatus of claim 2, wherein the at least one electrode element further comprises a hydrogel or a conductive adhesive on the first surface of the dielectric layer.

15. The apparatus of claim 2, wherein the at least one electrode element further comprises a metal layer on the second surface of the dielectric layer.

16. The apparatus of claim 1, wherein the first surface of the dielectric layer is non-planar, the second surface of the dielectric layer is substantially planar, and
    wherein a distance between the non-planar first surface and the substantially planar second surface is nonuniform and varies by less than or equal to 30%.

17. An apparatus for delivering tumor treating fields to a subject's body, the apparatus comprising:
    an array of connected electrode elements to be located on a subject's body and able to deliver tumor treating fields to the subject's body,
    wherein at least one electrode element of the array comprises a ceramic disk,
    wherein the ceramic disk has a first surface to face the subject's body and a second surface opposite the first surface, and
    wherein the ceramic disk has a nonuniform thickness.

18. The apparatus of claim 17, wherein, when viewed in cross-section, the first surface of the ceramic disk has a nonuniform surface.

19. An apparatus for delivering tumor treating fields to a subject's body, the apparatus comprising:
    a transducer to be located on a subject's body and able to deliver tumor treating fields to the subject's body,
    wherein the transducer comprises one or more electrode elements having a first surface to face the subject's body and a second surface opposite the first surface, and
    wherein at least one of the electrode elements comprises a polymer film having a first surface to face the subject's body and a second surface opposite the first surface, and wherein the polymer film has a nonuniform thickness.

20. The apparatus of claim 19, wherein, when viewed in cross-section, the first surface of the polymer film has a nonuniform surface.

* * * * *